United States Patent
Ono et al.

(10) Patent No.: US 9,148,631 B2
(45) Date of Patent: Sep. 29, 2015

(54) DEFECT INSPECTION METHOD AND DEVICE THEREFOR

(75) Inventors: Makoto Ono, Yokohama (JP); Takafumi Chida, Chigasaki (JP); Takehiro Hirai, Ushiku (JP); Masakazu Kanezawa, Shiroi (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 387 days.

(21) Appl. No.: 13/881,378

(22) PCT Filed: Oct. 26, 2011

(86) PCT No.: PCT/JP2011/074721
§ 371 (c)(1),
(2), (4) Date: May 30, 2013

(87) PCT Pub. No.: WO2012/057230
PCT Pub. Date: May 3, 2012

(65) Prior Publication Data
US 2013/0235182 A1    Sep. 12, 2013

(30) Foreign Application Priority Data
Oct. 28, 2010    (JP) ................................ 2010-242181

(51) Int. Cl.
    H04N 7/18        (2006.01)
    H01J 37/28       (2006.01)
    G01N 23/225      (2006.01)

(52) U.S. Cl.
CPC ............ *H04N 7/18* (2013.01); *G01N 23/2251* (2013.01); *H01J 37/28* (2013.01); *G01N 2223/3301* (2013.01); *G01N 2223/418* (2013.01); *G01N 2223/611* (2013.01); *H01J 2237/21* (2013.01); *H01J 2237/2811* (2013.01); *H01J 2237/2815* (2013.01); *H01J 2237/2817* (2013.01)

(58) Field of Classification Search
None
See application file for complete search history.

(56) References Cited

U.S. PATENT DOCUMENTS

| 6,614,923 B1 | 9/2003 | Shishido et al. |
| 2009/0206259 A1 | 8/2009 | Obara et al. |
| 2011/0194101 A1* | 8/2011 | Tachizaki et al. ............... 356/72 |

FOREIGN PATENT DOCUMENTS

| JP | 5-003013 | 1/1993 |
| JP | 11-194154 | 7/1999 |
| JP | 2005-285746 | 10/2005 |
| JP | 2009-009867 | 1/2009 |
| JP | 2009-194272 | 8/2009 |

OTHER PUBLICATIONS

Seungyong Lee et al. Scattered Data Interpolation with Multilevel B-Splines, IEEE Transactions on Visualization and Computer Graphics, Jul.-Sep. 1997, pp. 228-224, vol. 3, No. 3.

\* cited by examiner

*Primary Examiner* — Dave Czekaj
*Assistant Examiner* — Nam Pham
(74) *Attorney, Agent, or Firm* — Baker Botts L.L.P.

(57) ABSTRACT

In imaging a sample using an electron microscope, in order to reduce a time for focusing, a scanning range of a Z coordinate is reduced to complete focusing by obtaining SEM images such that: for a first predetermined number of portions, focal positions of an electron beam in obtaining each SEM image are moved in a predetermined range; then, a curved surface shape of the surface of the sample is estimated by using information relating to the focal positions of the electron beam in the first predetermined number of portions; after the images are taken, the range in which the focal positions of the electron beam are moved for scanning the electron beam on the surface of the sample is made to be narrower than the predetermined range by using the curved surface information estimated, thereby performing scanning to take the images of the sample.

11 Claims, 13 Drawing Sheets

| Point | x | y |
|---|---|---|
| 1 | 81.4 | 46.2 |
| 2 | 107.3 | 46.2 |
| 3 | 133.3 | 46.2 |
| 4 | 159.2 | 46.2 |
| 5 | 185.1 | 46.2 |
| 6 | 81.4 | 59.9 |
| 7 | 107.3 | 59.9 |
| 8 | 133.25 | 59.9 |
| 9 | 159.2 | 59.9 |
| 10 | 185.1 | 59.9 |
| 11 | 55.5 | 78.5 |
| 117 | 107.3 | 272.2 |
| 118 | 133.2 | 272.2 |
| 119 | 159.2 | 272.2 |
| 120 | 107.3 | 285.9 |
| 121 | 133.2 | 285.9 |
| 122 | 159.15 | 285.9 |

FIG. 8

| Point | x | y | |
|---|---|---|---|
| 15 | 159.2 | 78.5 | |
| 17 | 211 | 78.5 | |
| 37 | 55.5 | 124.5 | |
| 50 | 159.2 | 143.1 | |
| 57 | 81.4 | 156.75 | |
| 59 | 133.25 | 156.75 | 810 |
| 62 | 211 | 156.8 | |
| 89 | 133.2 | 207.6 | |
| 103 | 55.5 | 239.9 | |
| 117 | 107.3 | 272.2 | |
| 1 | 81.4 | 46.2 | |
| 2 | 107.3 | 46.2 | |
| 114 | 159.15 | 253.6 | |
| 115 | 185.1 | 253.6 | |
| 116 | 211 | 253.6 | |
| 118 | 133.2 | 272.2 | |
| 119 | 159.2 | 272.2 | |
| 120 | 107.3 | 285.9 | |
| 121 | 133.2 | 285.9 | |
| 122 | 159.15 | 285.9 | |

Columns: 801 (Point), 802 (x), 803 (y)

IMAGE ACQUISITION ORDER ↓

FIG. 9

| Point | x | y | z |
|---:|---:|---:|---:|
| 15 | 159.2 | 78.5 | -65 |
| 17 | 211 | 78.5 | -4 |
| 37 | 55.5 | 124.5 | -20 |
| 50 | 159.2 | 143.1 | 89 |
| 57 | 81.4 | 156.75 | 93.5 |
| 59 | 133.25 | 156.75 | 74.5 |
| 62 | 211 | 156.8 | -95 |
| 89 | 133.2 | 207.6 | -108 |
| 103 | 55.5 | 239.9 | -51 |
| 117 | 107.3 | 272.2 | 70 |
| 1 | 81.4 | 46.2 | |
| 2 | 107.3 | 46.2 | |
| 114 | 159.15 | 253.6 | |
| 115 | 185.1 | 253.6 | |
| 116 | 211 | 253.6 | |
| 118 | 133.2 | 272.2 | |
| 119 | 159.2 | 272.2 | |
| 120 | 107.3 | 285.9 | |
| 121 | 133.2 | 285.9 | |
| 122 | 159.15 | 285.9 | |

Column headers labeled: 801, 802, 803, 901

| Point | x | y | z | z' |
|---|---|---|---|---|
| 15 | 159.2 | 78.5 | −65 | −65.0 |
| 17 | 211 | 78.5 | −4 | −4.0 |
| 37 | 55.5 | 124.5 | −20 | −20.0 |
| 50 | 159.2 | 143.1 | 89 | 89.0 |
| 57 | 81.4 | 156.75 | 93.5 | −93.5 |
| 59 | 133.25 | 156.75 | 74.5 | 74.5 |
| 62 | 211 | 156.8 | −95 | −95.0 |
| 89 | 133.2 | 207.6 | −108 | −108.0 |
| 103 | 55.5 | 239.9 | −51 | −51.0 |
| 117 | 107.3 | 272.2 | 70 | 70.0 |
| 1 | 81.4 | 46.2 | | −35.7 |
| 2 | 107.3 | 46.2 | | −43.9 |
| 114 | 159.15 | 253.6 | | −24.1 |
| 115 | 185.1 | 253.6 | | −24.8 |
| 116 | 211 | 253.6 | | −26.8 |
| 118 | 133.2 | 272.2 | | 42.4 |
| 119 | 159.2 | 272.2 | | 7.2 |
| 120 | 107.3 | 285.9 | | 82.2 |
| 121 | 133.2 | 285.9 | | 61.3 |
| 122 | 159.15 | 285.9 | | 27.5 |

DEFECT INSPECTION METHOD AND DEVICE THEREFOR

BACKGROUND

The present invention relates to a defect inspection method and a defect inspection device used to inspect the quality of devices such as a semiconductor product, a magnetic head, a magnetic disk, a solar battery, an optical module, a light emitting diode, or a liquid crystal display panel, each of which is formed by repeating film formation, resist coating, exposure, development, etching, and the like on a substrate. Such a defect inspection method and a defect inspection device, for example, are used to inspect the dimension of a formed pattern, and the size and shape of a defect that has occurred, and the like. The present invention particularly relates to a defect inspection method and a defect inspection device which use a digital camera for an electron microscope or an optical microscope.

In recent years, electron microscopes are widely used to inspect the qualities of semiconductor products, magnetic heads, magnetic disks, solar batteries, optical modules, light emitting diodes, liquid crystal display panels, and the like, for example, to inspect a dimension of a formed pattern and the size and shape of a defect occurred.

In order to observe a pattern or a defect on a substrate using an electron microscope, a stage that holds thereon a substrate to be observed is moved so that specified XY coordinates are located near the center of an image. Next, a Z coordinate of the stage is moved so that the pattern or the defect is focused, and the image is acquired.

JP-A-2009-194272 (Patent Document 1) describes a method for registering an offset, called a focus map, of a Z coordinate in order to shorten a scanning range of the Z coordinate (in the direction of a normal to a stage surface on which a substrate is placed) and performing focusing the offset as a standard. In this method, a Z coordinate that causes a focal point to be adjusted to each of various positions on a certain substrate is measured, and a curved surface is approximated for measured XYZ coordinate groups, and the approximated curved surface is registered in an electron microscope as a focus map. Next, when another substrate is observed using the electron microscope, a Z coordinate that causes the focal point to be adjusted to certain XY coordinates is assumed to be close to the Z coordinate corresponding to the XY coordinates of the registered focus map, the Z coordinate is moved around the assumed Z coordinate, and focusing is performed.

SUMMARY

In order to observe a pattern or a defect on a substrate using an electron microscope, it is necessary to slowly move a Z coordinate in order to perform focusing while a depth of field of the electron microscope is shallow. Taking a long time to perform focusing is a problem to be solved.

In the method described in Patent Document 1, when an assumption that Z coordinates corresponding to the XY coordinates are close to each other between substrates is not sufficiently satisfied, there is a problem that focusing is delayed.

The present invention provides a defect inspection method and a defect inspection device, which can reduce a scanning range in which a Z coordinate is moved in order to perform focusing, thereby reducing the time to perform the focusing as a result of the shortening, even if Z coordinates corresponding to XY coordinates are not close to each other between substrates.

In the method described in Patent Document 1, a cumbersome task of measuring Z coordinates corresponding to many XY coordinates for an arbitrary substrate and registering a focus map is required. The present invention, however, provides a defect inspection method and a defect inspection device, which do not need such a cumbersome task.

In order to solve the aforementioned problems, according to the present invention, a defect inspection device includes: a scanning electron microscope that irradiates a sample with a focused electron beam, performs scanning, and thereby acquires an SEM image of the sample; image processing unit which processes the SEM image acquired by imaging the sample with the scanning electron microscope; output unit which outputs, on a screen, a result of processing the SEM image of the sample with the image processing unit; and control unit which controls the scanning electron microscope, the image processing unit, and the output unit. In the defect inspection device, when the control unit controls the scanning electron microscope for sequentially imaging a plurality of portions on the sample, the control unit causes the scanning electron microscope: in a first predetermined number of portions, to perform the scanning by moving a focal point of the electron beam in a normal direction relative to a surface of the sample in a predetermined range; to adjust the focal point of the electron beam to the surface of the sample; and to image the sample; then, to estimate a curved surface shape of the surface of the sample by using information about positions to which the focal point of the electron beam has been adjusted on the surface of the sample in the first predetermined number of portions; after imaging the sample in the first predetermined number of portions, to use information about the estimated curved surface to perform the scanning by moving the focal point of the electron beam in the normal direction in a narrower range than the predetermined range for the scanning that has been performed in the first predetermined number of portions in order to adjust the focal point of the electron beam to the surface of the sample; to adjust the focal point of the electron beam to the surface of the sample; and to image the sample.

In addition, in order to solve the aforementioned problems, according to the present invention, a defect inspection method comprising the steps of: sequentially acquiring SEM images of a plurality of portions on a sample by irradiating the plurality of portions on a sample with an electron beam focused by a scanning electron microscope to perform scanning; processing the SEM images obtained by sequentially imaging the plurality of portions on the sample with the scanning electron microscope and inspecting the sample; and outputting a result of processing the SEM images of the sample. In the defect inspection method, the sequential acquisition of the SEM images of the plurality of portions on the sample with the scanning electron microscope includes the steps of: performing the scanning for a first predetermined number of portions by moving a focal point of the electron beam in a normal direction relative to a surface of the sample in a predetermined range, adjusting the focal point of the electron beam to the surface of the sample, and imaging the sample; estimating a curved surface shape of the surface of the sample by using information about positions to which the focal point of the electron beam has been adjusted on the surface of the sample in the first predetermined number of portions; and after imaging the sample in the first predetermined number of portions, using information about the estimated curved surface to perform the scanning by moving the focal point of the electron beam in the normal direction in a narrower range than the predetermined range for the scanning that has been performed in the first predetermined number of portions in order to adjust the focal point of the electron beam to the surface of the sample, adjusting the focal point of the electron beam to the surface of the sample, and imaging the sample.

Furthermore, in order to solve the aforementioned problems, according to the present invention, a defect inspection method comprising the steps of: sequentially acquiring SEM images of a plurality of portions on a sample by sequentially performing, on a plurality of portions of the surface of the sample, scanning with a focal point of an electron beam focused by a scanning electron microscope, the focal point adjusted to a surface of a sample, and imaging the sample; processing the sequentially acquired SEM images of the plurality of portions on the sample and inspecting the sample; and outputting results of the inspection. In the defect inspection method, the adjusting of the focal point of the electron beam focused by the scanning electron microscope on the surface of the sample includes the steps of: performing the scanning in a first predetermined number of portions by moving the focal point of the electron beam in a normal direction relative to the surface of the sample in a predetermined range, adjusting the focal point of the electron beam to the surface of the sample, and imaging the sample; after imaging the sample in the first predetermined number of portions, performing the scanning by moving the focal point of the electron beam in a narrower range than the predetermined range in which scanning has been performed in the first predetermined number of portions using information indicating that the focal point of the electron beam has been adjusted to the surface of the sample for each of the first predetermined number of portions, adjusting the focal point of the electron beam on the surface of the sample, and imaging the sample.

According to the present invention, the defect inspection methods and the defect inspection device can reduce the scanning range of the Z coordinate to be moved in order to perform focusing for various substrates and can thereby reduce the time to complete the focusing. In addition, Z coordinates corresponding to many XY coordinates are measured for an arbitrary substrate in advance, and an image can be acquired without a cumbersome task of registering a focus map.

These features and advantages of the invention will be apparent from the following more particular description of preferred embodiments of the invention, as illustrated in the accompanying drawings.

BRIEF DESCRIPTION OF THE DRAWINGS

FIG. 8 is a diagram illustrating an example of image acquisition coordinate data after alignment.

FIG. 9 is a diagram illustrating an example of image acquisition coordinate data after images of the initial image acquisition coordinate groups are acquired.

DESCRIPTION OF THE PREFERRED EMBODIMENTS

Hereinafter, embodiments of the present invention are described in detail with reference to the accompanying drawings.

First Embodiment

Figure 1:
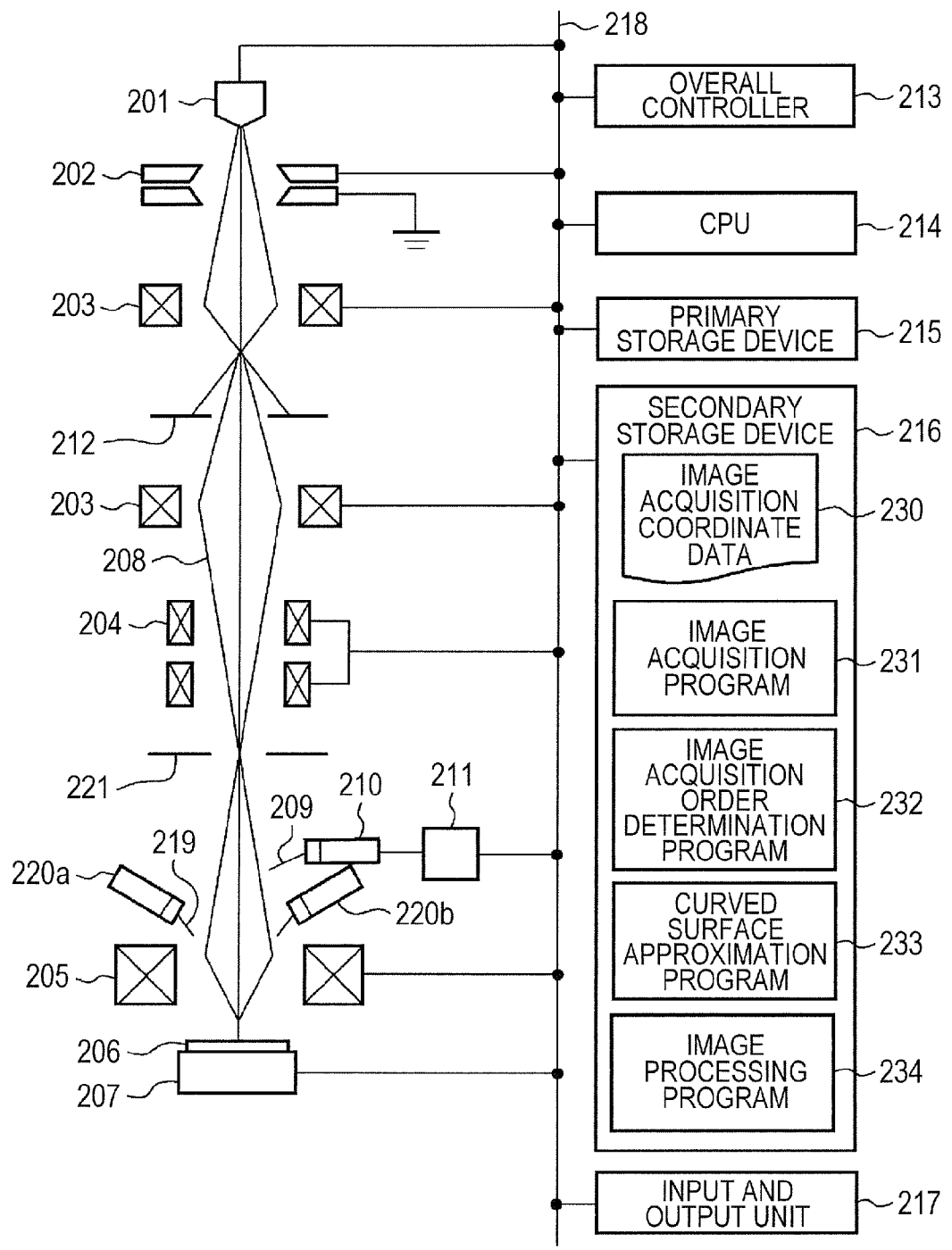
FIG. 1 is a block diagram illustrating an example of an outline of an electron microscope device.

FIG. 1 is a diagram illustrating an example of an outline of a scanning electron microscope (SEM) as an example of a defect inspection method and defect inspection device according to the first embodiment. The scanning electron microscope has an electron source 201 for generating a primary electron 208, an acceleration electrode 202 for accelerating the primary electron, a focusing lens 203 for focusing the primary electron, an aperture 212 for narrowing a beam, a deflector 204 for two-dimensionally scanning and deflecting the primary electron, a blanking electrode 221 for temporarily stopping irradiation of a substrate 206 with the beam, and an objective lens 205 for focusing the primary electron on the substrate 206 such as a wafer. Reference numeral 207 indicates a driving stage that holds the substrate 206 thereon. Reference numeral 210 indicates a detector that detects a secondary electron 209 generated from the substrate 206. Reference symbols 220a and 220b indicate reflected electron detectors that detect a reflected electron 219. In FIG. 1, the reflected electron detectors 220a and 220b face to each other and detect different components of the reflected electron 219. Reference numeral 211 indicates a digital converter (A/D converter) that digitalizes the detected signals. These parts are connected to an overall controller 213 through a bus 218.

The scanning electron microscope according to the present embodiment further includes a central processing unit (CPU) 214, a primary storage device 215, a secondary storage device 216, and an input and output unit 217 that is a keyboard, a mouse, a display, a printer, a network interface, or the like. In addition, image acquisition coordinate data 230, an image acquisition program 231, an image acquisition order determination program 232, a curved surface approximation program 233, an image processing program 234, and the like are stored in the secondary storage device 216. In the image acquisition coordinate data 230, coordinate groups from which images are to be acquired in a surface of the substrate 206 are described. The image acquisition program 231 is used to cause the driving stage to move and acquire an image. The image acquisition order determination program 232 is used to align the image acquisition coordinate data and determine the order of acquiring images. The curved surface approximation program 233 is used to approximate a curved surface such as a B-spline surface or a response surface from XY coordinates from which the images are acquired and Z coordinates that cause a focal point to be adjusted to the XY coordinates. The image processing program 234 is used to process the acquired images (SEM images), extract a defect, calculate an image characteristic amount of the defect, classify the defect, and calculate dimensions of patterns included in the acquired processed images and a distance between the patterns. These programs are read from the secondary storage device 216 into the primary storage device 215 and run by the central processing unit (CPU) 214.

Figure 2:
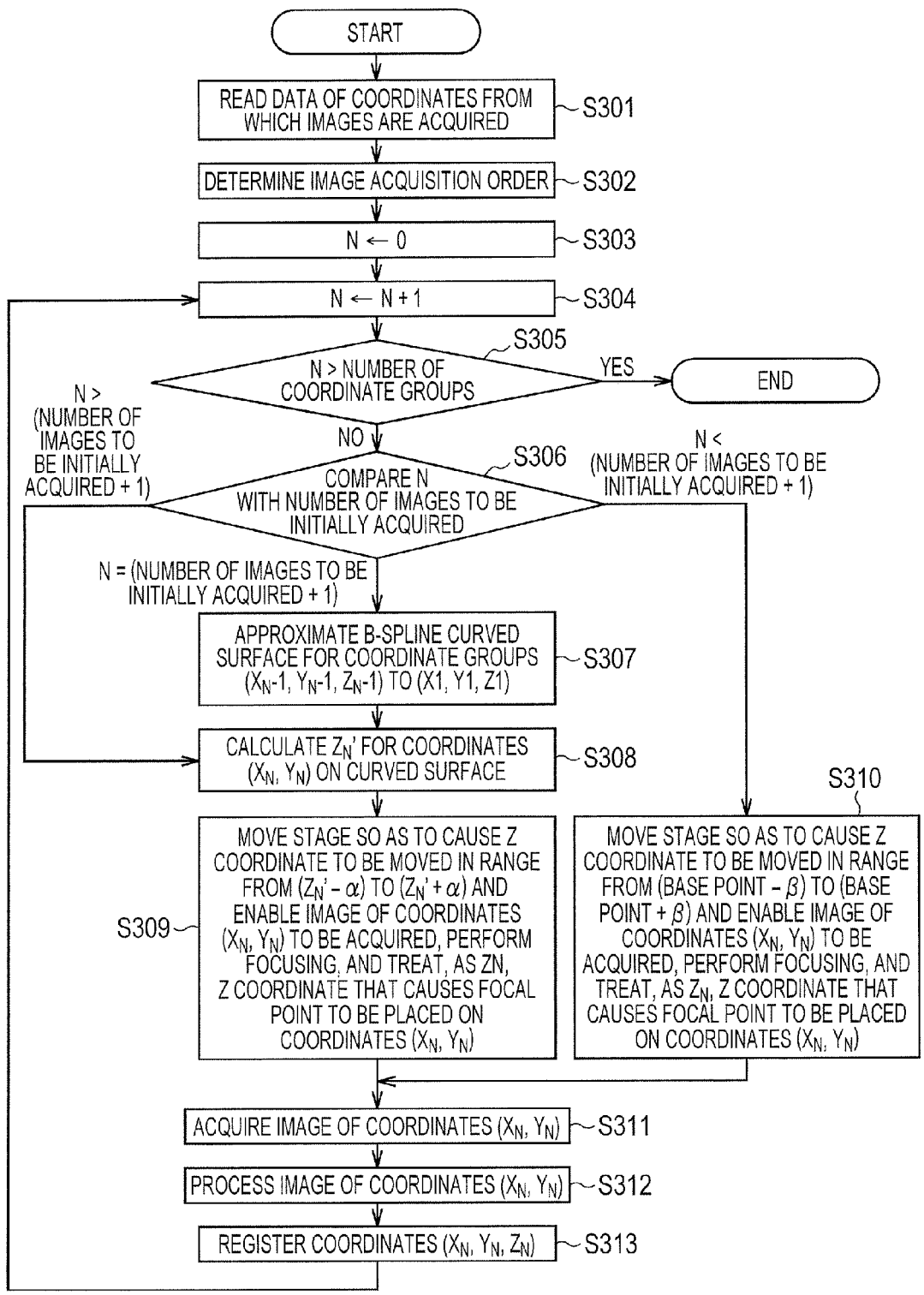
FIG. 2 is a flow diagram illustrating an example of a flowchart of an image acquisition program.

FIG. 2 illustrates an example of a flowchart of the image acquisition program 231. According to the image acquisition program 231, the image acquisition coordinate data 230 is read in step S301, and the order of acquiring images of the coordinate groups described in the read image acquisition coordinate data 230 is determined in step S302. The image acquisition coordinate data 230 read in step S301 may be design data (CAD data) about a circuit pattern formed on the substrate 206 or positional information about a defect (pattern defect, foreign material defect, or the like) inspected and detected by another inspection device.

In this flowchart, the order of acquiring the images of the coordinate groups is defined as the order of coordinates (X1, Y1), (X2,Y2), . . . , and (XN, YN). In addition, a Z coordinate that causes the focal point to be adjusted to the coordinates (XN, YN) in order to acquire an image of the coordinates (XN, YN) is defined as ZN, and the three-dimensional coordinates are defined as (XN, YN, ZN). Next, a variable N is substituted with zero in step S303, and the variable N is incremented by 1 in step S304. If the variable N exceeds the number of the coordinate groups described in the image acquisition coordinate data 230 in conditional branching step S305, the program is terminated.

On the other hand, if the variable N does not exceed the number of the coordinate groups described in the image acquisition coordinate data 230 in conditional branching step S305, the process proceeds to step S306. In step S306, the variable N is compared with the number of the images to be initially acquired, which is specified in step S302, and the process proceeds to any of steps S307, S308, and S310. If the variable N is smaller than a value obtained by adding 1 to the number of the images to be initially acquired, the process proceeds to step S310. If the variable N is equal to the value obtained by adding 1 to the number of the images to be initially acquired, the process proceeds to step S307. If the variable N is larger than the value obtained by adding 1 to the number of the images to be initially acquired, the process proceeds to step S308.

Step S310 is performed when the variable N is in a range of 1 to the number of the images to be initially acquired. In step S310, the stage is moved so that an image of the coordinates (XN, YN) can be acquired, while performing the scanning in a range of (a base point−β) to (the base point+β) of Z coordinate, and the focusing is completed. The base point means an estimated value of an average Z coordinate of the surface of the substrate, and β is a fixed value that is larger than a described later. Step S307 is performed when the variable N is equal to the value obtained by adding 1 to the number of the images to be initially acquired. In step S307, a B-spline surface is approximated for a number N of three-dimensional coordinates from (X1,Y1, Z1) to (XN−1, YN−1, ZN−1), and the approximated curved surface is treated as a focus map.

In step S308, a value ZN' for coordinates (XN, YN) of the approximated curved surface is calculated. The value ZN' is an estimated value of a Z coordinate that is estimated to cause the focal point to be adjusted to the coordinates (XN, YN) in order to acquire an image of the coordinates (XN, YN).

In step S309, the stage is moved so as to enable an image of the coordinates (XN, YN) to be acquired, while performing the scanning in a scanning range of (ZN'−α) to (ZN'+α) of Z coordinate, and the focusing is completed. The Z coordinate that causes the focal point to be adjusted to the coordinates (XN, YN) is regarded as ZN. The value α can be set to a smaller value than the value β by generating the focus map and calculating ZN'. As a result, the scanning range of the Z coordinate can be reduced, and the time to perform the focusing can be reduced. In step S311, an image of the coordinates (XN, YN) to which the focal point is adjusted is acquired. In step S312, the acquired image is processed according to the image processing program 234 so that image processing of detecting a defect from the acquired image of the coordinates (XN, YN), extracting a characteristic amount of the defect and classifying the defect, or image processing of calculating a size of the defect or a pattern, or calculating a distance between patterns from a characteristic amount of the image is performed. In step S313, the three-dimensional coordinates (XN, YN, ZN) are registered in the secondary storage device 216 in order to generate or update the focus map in step S307. Then, the process returns to step S304.

Figure 14:
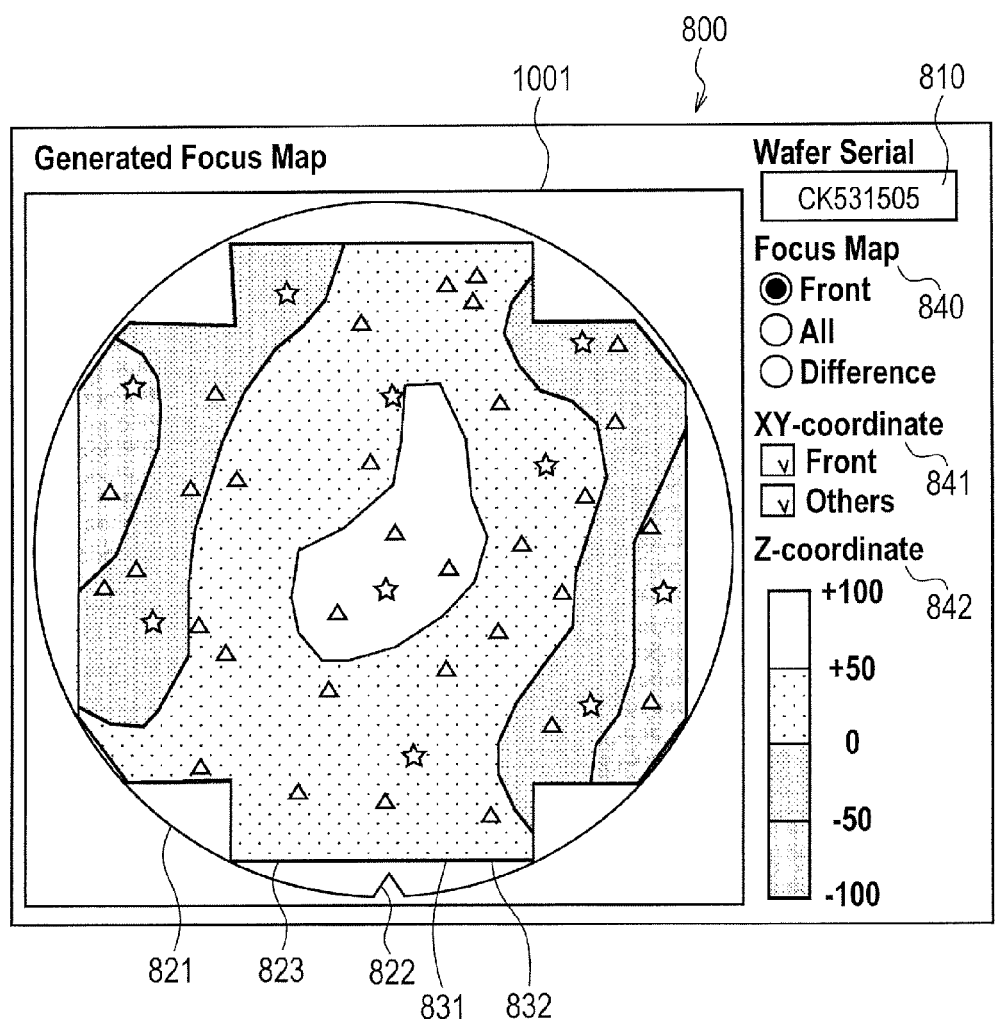
FIG. 14 is a front view of a screen showing an example of a graphical user interface displaying an approximated curved surface.

FIG. 14 illustrates an example of a graphical user interface for displaying the curved surface approximated in step S307. A graphical user interface 800 has a part 820 for displaying the approximate curved surface or the focus map, a part 810 for displaying the number of the wafer to be inspected, a part 840 for selecting the type of the focus map to be displayed, a part 841 for selecting a defect to be displayed simultaneously with the focus map, and a part 842 for displaying a scale for the display of the focus map. In the part 820 for displaying the focus map, an outer frame 821 of the wafer is displayed, and a notch 822 is displayed in order to recognize the orientation of the wafer. Since the focus map is calculated not for an overall surface of the wafer but for only a region on which products such as an integrated circuit are formed, the region is displayed as 823.

Colors are added to the region 823 in order to recognize bias of the focus map, and contour lines are depicted in the region 823. The definition of the color addition is displayed as the scale 842. In order to display the focus map, one of "Front", "All", and "Difference" is selected in the selection part 840. If "Front" is selected, the curved surface approximated in step S307 is displayed as the focus map on the basis of initial image acquisition coordinate groups. If "All" is selected, a B-spline surface is approximated from all input coordinate groups in the same manner as step S307, and the result of the approximation is displayed.

If "Difference" is selected, a result obtained by calculating, for each of coordinate groups, a difference between the curved surface displayed when "Front" is selected and the curved surface displayed when "All" is selected is displayed. On this graphical user interface, the focus map and coordinates from which images are acquired can be simultaneously displayed. Whether or not simultaneously displaying the coordinates from which the images are acquired is selected using the selection part 841. Regarding the selection method, there are four cases: the case where both "Front" and "Others" are not selected, the case where only "Front" is selected, the case where only "others" is selected, and the case where both "Front" and "Others" are selected. If "Front" is selected, initial image acquisition coordinate groups that are indicated by star signs 831 are displayed with overlapped with the focus map. If "Others" is selected, all other coordinates excluding initial image acquisition coordinate groups indicated by triangles 832 are displayed.

Figure 15:
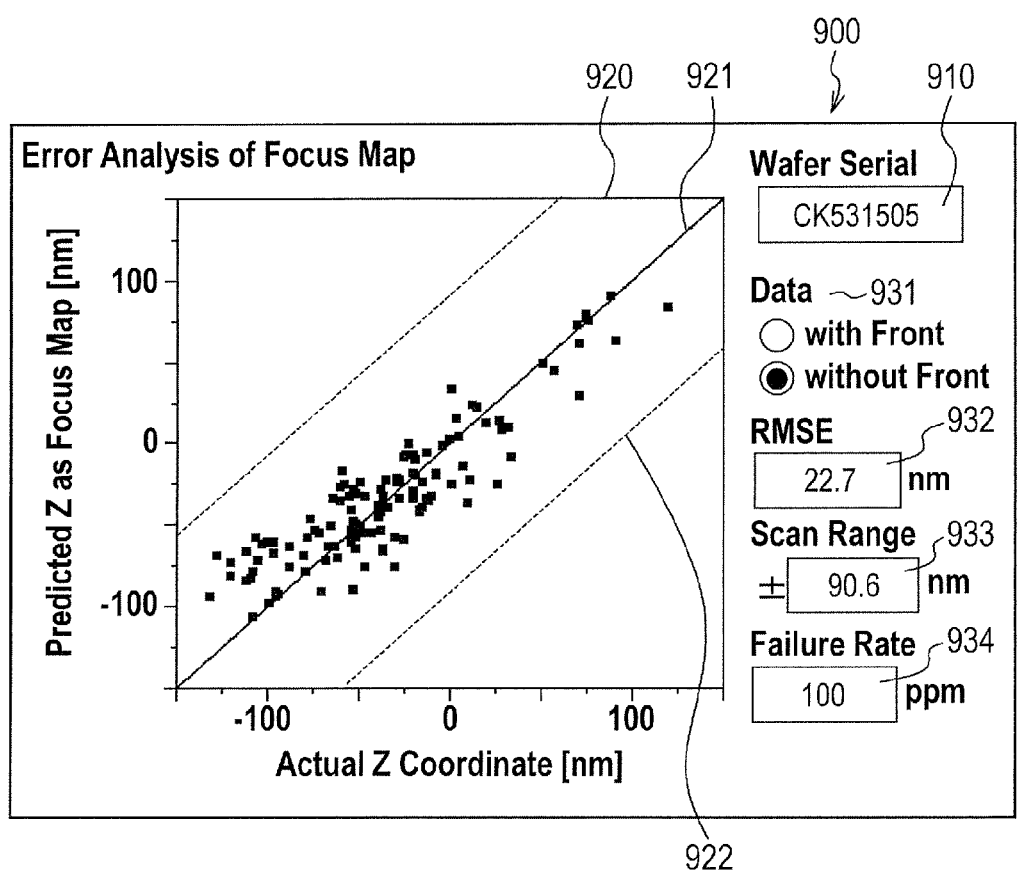
FIG. 15 is a front view of a screen showing an example of a graphical user interface displaying differences between the curved surface and actual measured values.

FIG. 15 illustrates an example of a graphical user interface that displays differences between Z coordinates when the curved surface is approximated in step S307 and Z coordinates when focusing is performed for acquisition of images.

A graphical user interface 900 has a graph display part 920, a part 910 for displaying the number of the wafer to be inspected, a part 931 for selecting data to be displayed, a part 932 for displaying, as a root mean square error (RMSE) represented by Equation 1, differences between Z coordinates of the approximated curved surface or focus map and the Z coordinates when the focusing is actually performed for the acquisition of the images, a part 933 for displaying and entering a value of a scanning range a for the focusing to be performed in step S309, and a part 934 for displaying and entering a result of estimating a probability of a focusing error in which the Z coordinate at which the focusing is completed is not in the scanning range of (ZN'−α) to (ZN'+α) in step S309.

[Equation 1]

$$RMSE = \sqrt{\frac{\sum_{N=1}^{Number\ of\ coordinates}(Z_N - Z'_N)^2}{Number\ of\ coordinates}}$$ (Equation 1)

In the graph display part 920, the abscissa indicates a Z coordinate when the focusing is completed for acquisition of an image, and the ordinate indicates a value estimated from the focus map. The graph display part 920 displays a distribution diagram in which a point is added for each group of coordinates from which images are acquired. A straight line 921 is a straight line on which values of the ordinate and abscissa are the same. It is apparent that the closer to the straight line 921, the higher the accuracy of the focus map. A result that quantitatively indicates the accuracy is a value displayed in the RMSE display part 932. Two broken lines 922 that are drawn in the distribution diagram are straight lines that indicate +α and −α of the scanning range of the Z coordinate. The drawing of the broken lines 922 coordinates with a value entered in the part 933 for displaying and entering a value of α.

The original data from which the points are provided to the distribution diagram is determined by selecting any one of "with Front" and "without Front" in the data selection part 931. If "with Front" is selected, Z coordinates that correspond to all XY coordinates from which images are acquired are targets. The initial image acquisition coordinate groups for generation of the focus map are included in "with Front". If "without Front" is selected, Z coordinates that correspond to XY coordinates excluding the initial image acquisition coordinate groups from all coordinate groups from which images are acquired are targets.

A value of the part 933 for displaying and entering the value of α and a value of the part 934 for displaying and entering the probability of the focusing error coordinate with each other. For example, when the RMSE is 22.7 nanometers as illustrated in the example of the distribution diagram, if a value that is 3.99 times as large as 22.7 or 90.6 is entered, the probability of the error or the probability that a point is provided in the outside of the broken lines 922 is 100 ppm. This calculation is equivalent with that, on an assumption that the RMSE is equal to a standard deviation, α is 3.99 times the standard deviation. Specifically, a probability of being larger by +α or smaller by −α than a probability density function, indicated by Equation 2, of a normal distribution is a result calculated according to Equation 3. In Equation 2, σ is the standard deviation or the RMSE in this case, and μ is the average of differences between ZN' and ZN.

$$f(x) = \frac{1}{\sqrt{2\pi}\sigma} \exp\left(-\frac{'(x-\mu)^2}{2}\right)$$ (Equation 2)

$$\text{Probability of error} = \int_{-\infty}^{-\alpha} f(x)dx + \int_{\alpha}^{\infty} f(x)dx$$ (Equation 3)

Figure 3:
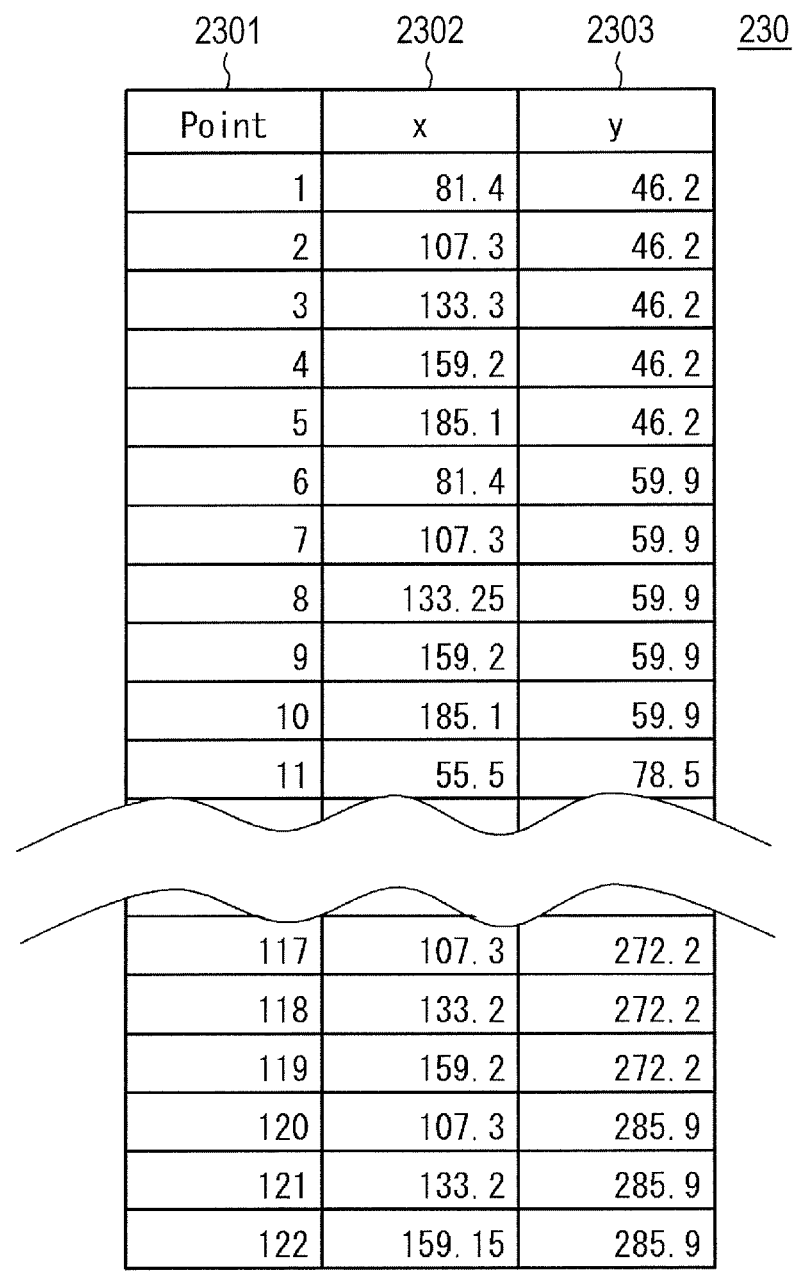
FIG. 3 is a diagram illustrating an example of image acquisition coordinate data.

FIG. 3 illustrates an example of the image acquisition coordinate data 230 read in S301. The image acquisition coordinate data 230 includes a plurality of XY coordinates, and serial numbers are added to the XY coordinates. Points 2301 indicated in the leftmost column are the serial numbers of the coordinates, X 2302 indicated in the second column indicates the X coordinates, and Y 2303 indicated in the third column indicates the Y coordinates. In this example, 122 coordinates are illustrated. The present invention, however, is not limited to the 122 coordinates. The number of coordinates is arbitrary as long as the number of the coordinates is two or more.

Figure 4:
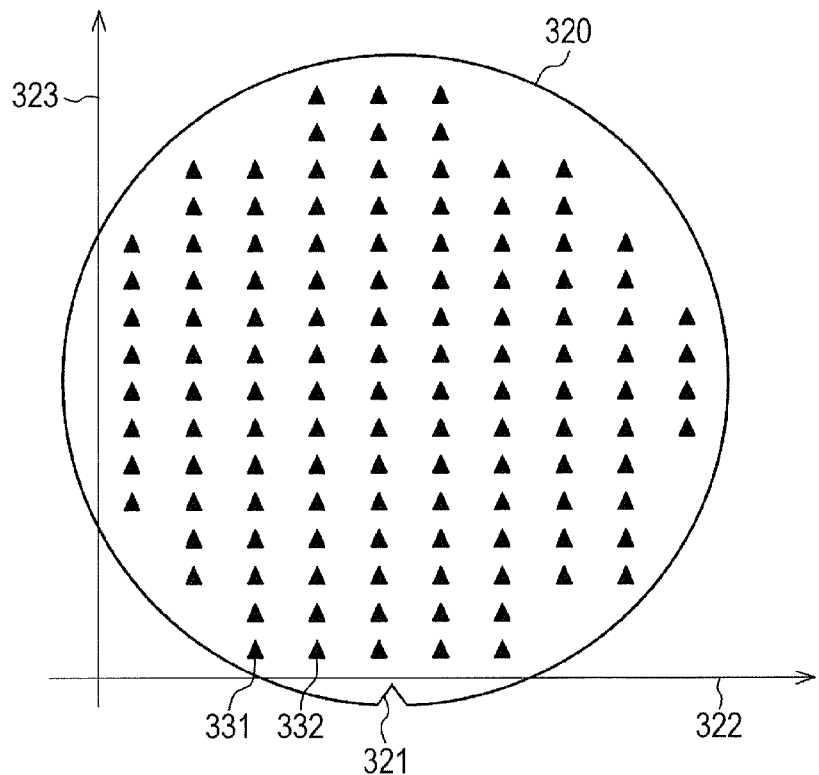
FIG. 4 is a plan view of a wafer, illustrating an example of a map including image acquisition coordinate data.

FIG. 4 illustrates an example in which the image acquisition coordinate data 230 illustrated in FIG. 3 is visually illustrated. A circular frame 320 indicates the substrate that has a notch 321 that is a standard of a coordinate system. In this example, when the notch 321 is located on the lower side, a lowermost end on which a semiconductor product, a magnetic head, or the like is formed is defined as an X axis, and a leftmost end is defined as a Y axis. The image acquisition coordinate data 230 is read onto the XY coordinate system, and black triangles indicate points of the coordinate groups. For example, a triangle 331 indicates coordinates (81.4, 46.2) of the serial number (point) 2301 (illustrated in FIG. 3) of 1, and a triangle 332 indicates coordinates (107.3, 46.2) of the serial number (point) 2301 (illustrated in FIG. 3) of 2.

Figure 5:
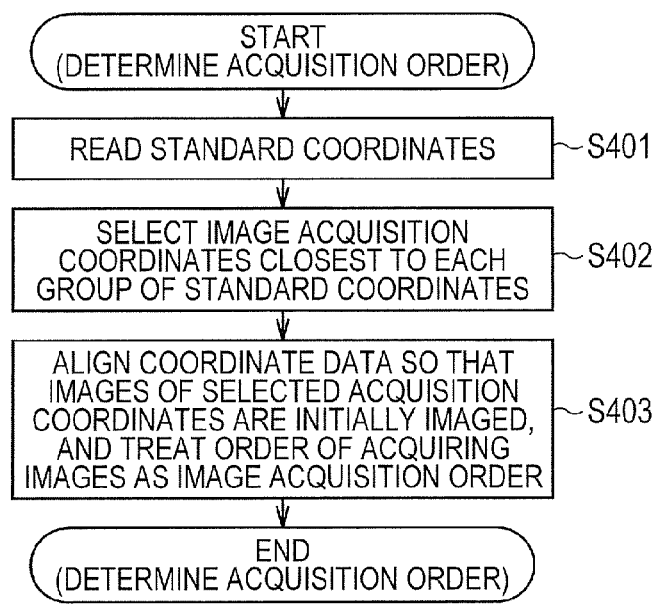
FIG. 5 is a flow diagram illustrating an example of a flowchart of an image acquisition order determination program.

FIG. 5 illustrates an example of a flowchart for step S302 of the image acquisition program described with reference to FIG. 2 or for the image acquisition order determination program 232 for determining the order of acquiring images. In step S401, standard coordinates that include a plurality of XY coordinates are read from the secondary storage device 216. The standard coordinates are coordinate groups for which Z coordinates are recommended to be measured in order to generate the focus map. In step S402, image acquisition coordinates that are closest to each of the standard coordinate groups read in step S401 are selected from the image acquisition coordinate data 230. In step S403, the image acquisition coordinate data is aligned so that images of the selected plurality of image acquisition coordinates are initially acquired, and the order of acquiring the images is treated as an image acquisition order.

Figure 6:
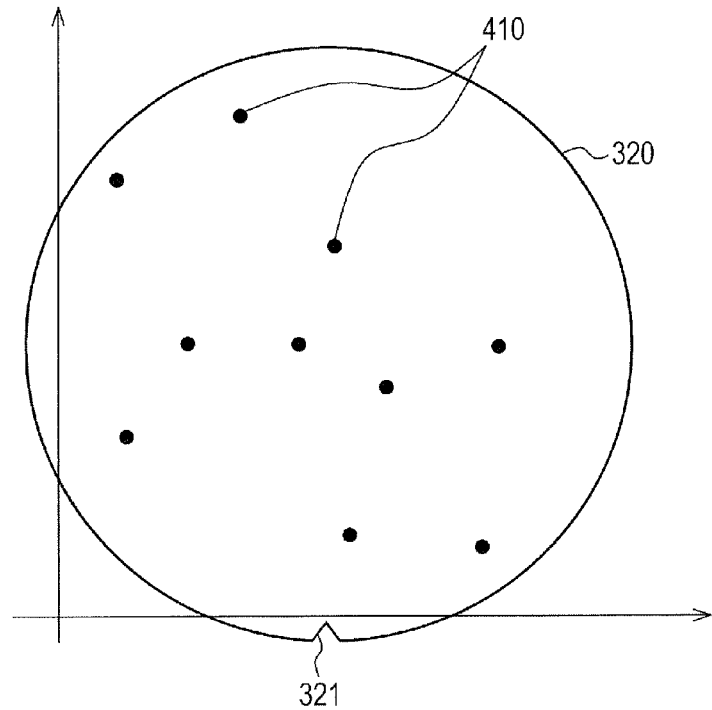
FIG. 6 is a plan view of the wafer, illustrating an example of standard coordinates.

FIG. 6 visually illustrates an example of the standard coordinates read in step S401 of the image acquisition order determination program 232. In this example, 10 points 410 are at the standard coordinates. The standard coordinates are preferably located near an edge portion of the wafer and distributed on the overall surface of the wafer. The standard coordinates may be registered in the secondary storage device 216 in advance, or set using the input and output unit 217 every time the substrate is observed. In this example, the 10 coordinates are illustrated as the standard coordinates. The standard coordinates, however, are not limited to the 10 coordinates. The number of the standard coordinates may be arbitrary as long as the number of the standard coordinates is two or more.

Figure 7:
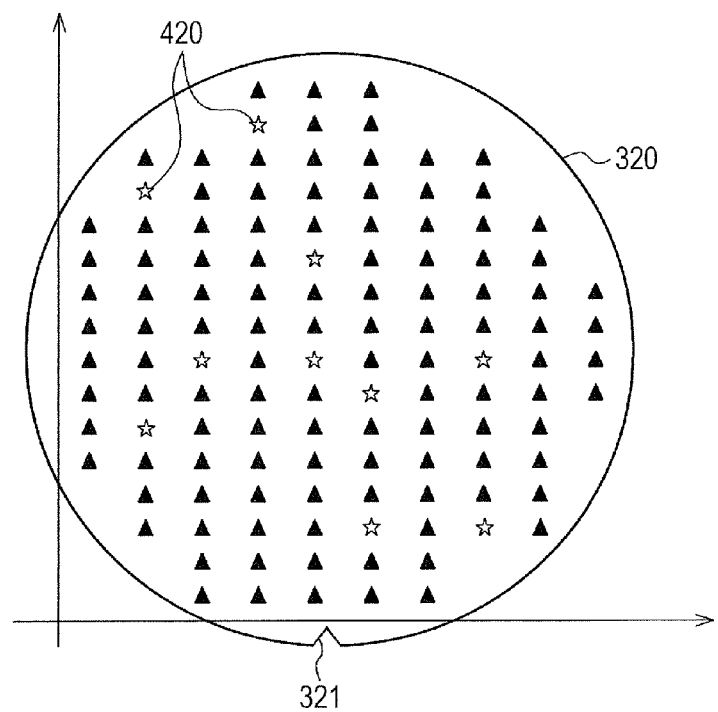
FIG. 7 is a plan view of the wafer, illustrating initial image acquisition coordinate groups.

FIG. 7 visually illustrates an example of the image acquisition coordinates selected in step S402 of the image acquisition order determination program 232. In this example, image acquisition coordinates positioned closest to the 10 points illustrated in FIG. 6 are selected from among the coordinate groups indicated by the triangles in FIG. 4. Ten points indicated by star signs 420 are the selected image acquisition coordinates.

FIG. 8 illustrates an example of the image acquisition order determined by the image acquisition order determination program 232. In this example, the 10 coordinates that are indicated by the star signs 420 in FIG. 7 and included in the image acquisition coordinate data 2301, 2302, and 2303 illustrated in FIG. 3 are described in a top portion. The coordinate groups indicated by the star signs 420 and described in the top portion are referred to as initial image acquisition coordinate groups 810.

FIG. 9 illustrates an example of the three-dimensional coordinates registered in step S312 of the image acquisition program 231 described with reference to FIG. 2. This example indicates results of completely acquiring images of all the points of the initial acquisition coordinate groups 810 illustrated in FIG. 8, or results of registering coordinates from (X1, Y1, Z1) to (X10, Y10, Z10). 10 Z coordinates from which images are completely acquired, or Z coordinates 901 at which the focusing is completed are added to image acquisition coordinate data 801, 802, and 803 aligned in the image acquisition order illustrated in FIG. 8.

Figure 10:
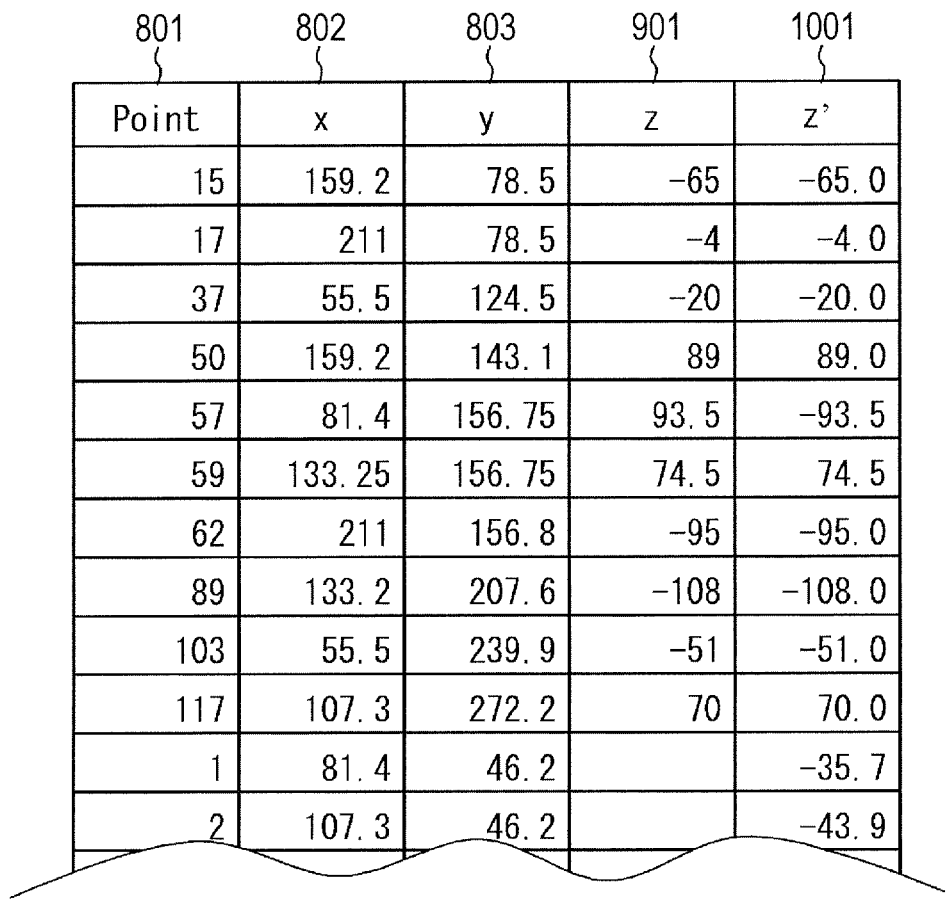
FIG. 10 is a diagram illustrating an example of image acquisition coordinate data after a curved surface is approximated.

FIG. 10 illustrates an example of results of approximating the curved surface by the curved surface approximation program 233 or results of step S307 of the image acquisition program 231 described with reference to FIG. 2. In FIG. 10, the results of approximating the B-spline surface relative to the results of registering the coordinates (X1, Y1, Z1) to (X10, Y10, Z10) are illustrated. The B-spline surface approximation is a method for generating a smooth, adjustable surface using positional vectors of 16 control points arranged in order and is widely used for a computer aided design (CAD) tool, as described in "S. Lee, G. Wolberg, S. Y. Shin: "Scattered Data Interpolation with Multilevel B-Splines", IEEE Transactions on Visualization and Computer Graphics, Vol. 3, No. 3 pages 228-244 (1997):" (Non-Patent Document 1). Z coordinates corresponding to XY coordinates on the approximated B-spline surface are indicated by Z' 1001 on the rightmost column of the table. In this example, the B-spline surface approximation is used. The present invention, however, is not limited to the B-spline surface. A response surface or a Bezier curved surface may be approximated.

Figure 11:
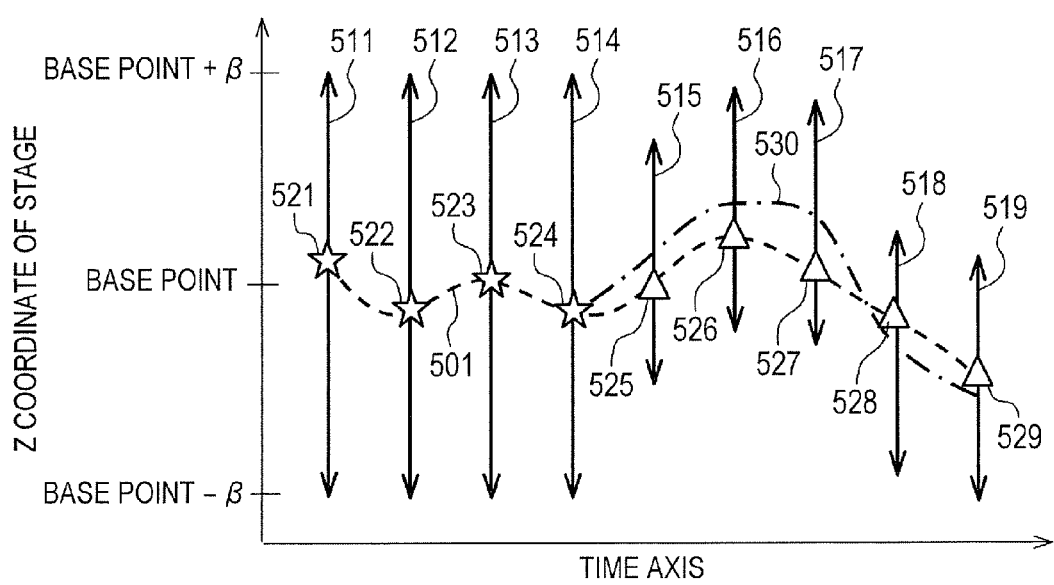
FIG. 11 is a graph illustrating an example of an outline diagram with respect to a time axis.

FIG. 11 is an example of a schematic diagram illustrating the state in which the scanning range of the Z coordinate that is moved for the focusing is changed by executing the image acquisition program described with referenced to FIG. 2. In this schematic diagram, the image acquisition coordinates are reduced to 9 coordinates for convenience of the sheet. The abscissa indicates a time axis, and the ordinate indicates a Z coordinate that is moved for the focusing. A broken line 501 indicates a Z coordinate of the surface of the substrate. Arrows from 511 to 519 that extend in a vertical direction indicate Z-directional ranges of the Z coordinate to be moved in order to adjust the focal point to the image acquisition coordinates.

After the image acquisition program is executed and the image acquisition order is determined, the Z coordinate is moved in the range indicated by the arrow 511 for coordinates from which an image is acquired first, and the focusing is performed. The center of the arrow 511 is a vertical position of the base point. The Z coordinate at which the focusing is completed is indicated by a star sign 521. Next, the Z coordinate is moved in the range indicated by the arrow 512 for coordinates from which an image is acquired second, and the focusing is performed. The center of the arrow 512 is a vertical position of the base point. The Z coordinate at which the focusing is completed is indicated by a star sign 522. Next, the Z coordinate is moved in the range indicated by the arrow 513 for coordinates from which an image is acquired third, and the focusing is performed. The center of the arrow 513 is a vertical position of the base point. The Z coordinate at which the focusing is completed is indicated by a star sign 523. Next, the Z coordinate is moved in the range indicated by the arrow 514 for coordinates from which an image is acquired fourth, and the focusing is performed. The center of the arrow 514 is a vertical position of the base point. The Z coordinate at which the focusing is completed is indicated by a star sign 524.

In the schematic diagram, the first to fourth image acquisition coordinates are initial coordinate groups. Next, a curved surface is approximated for the first to fourth image acquisition coordinates and the Z coordinates indicated by the star signs 521, 522, 523, and 524. Z coordinates of a curved surface approximated for the fifth to ninth image acquisition coordinates, or estimated values of Z coordinates at which the focusing is estimated to be completed for the fifth to ninth image acquisition coordinates, are indicated by an alternate long and short dashed line 530.

Next, a range of an arrow 515 is determined for the fifth image acquisition coordinates so that the alternate long and short dashed line 530 is located at the center of the arrow 515, the Z coordinate is moved, and the focusing is performed. The alternate long and short dashed line 530 crosses at the center of the arrow 515. A Z coordinate at which the focusing is completed is indicated by a triangle 525. Next, a range of an arrow 516 is determined for the sixth image acquisition coordinates so that the alternate long and short dashed line 530 is located at the center of the arrow 516, the Z coordinate is moved, and the focusing is performed. A Z coordinate at which the focusing is completed is indicated by a triangle 526. Next, a range of an arrow 517 is determined for the seventh image acquisition coordinates so that the alternate long and short dashed line 530 is located at the center of the arrow 517, the Z coordinate is moved, and the focusing is performed. A Z coordinate at which the focusing is completed is indicated by a triangle 527. Next, a range of an arrow 518 is determined for the eighth image acquisition coordinates so that the alternate long and short dashed line 530 is located at the center of the arrow 518, the Z coordinate is moved, and the focusing is performed. A Z coordinate at which the focusing is completed is indicated by a triangle 528. Next, a range of an arrow 519 is determined for the ninth image acquisition coordinates so that the alternate long and short dashed line 530 is located at the center of the arrow 519, the Z coordinate is moved, and the focusing is performed. A Z coordinate at which the focusing is completed is indicated by a triangle 529.

According to the present embodiment, a curved surface is approximated on the basis of focal point positional information about initial image acquisition coordinate groups, a Z-directional scanning range of which the center is on the curved surface is reduced, and whereby the focusing can be completed in a shorter time.

Second Embodiment

The first embodiment describes the example in which a curved surface is approximated only once when the acquisition of the images of the initial image acquisition coordinate groups are completed and the focus map is generated. The second embodiment describes an example in which the focus map is updated at any time.

Figure 12:
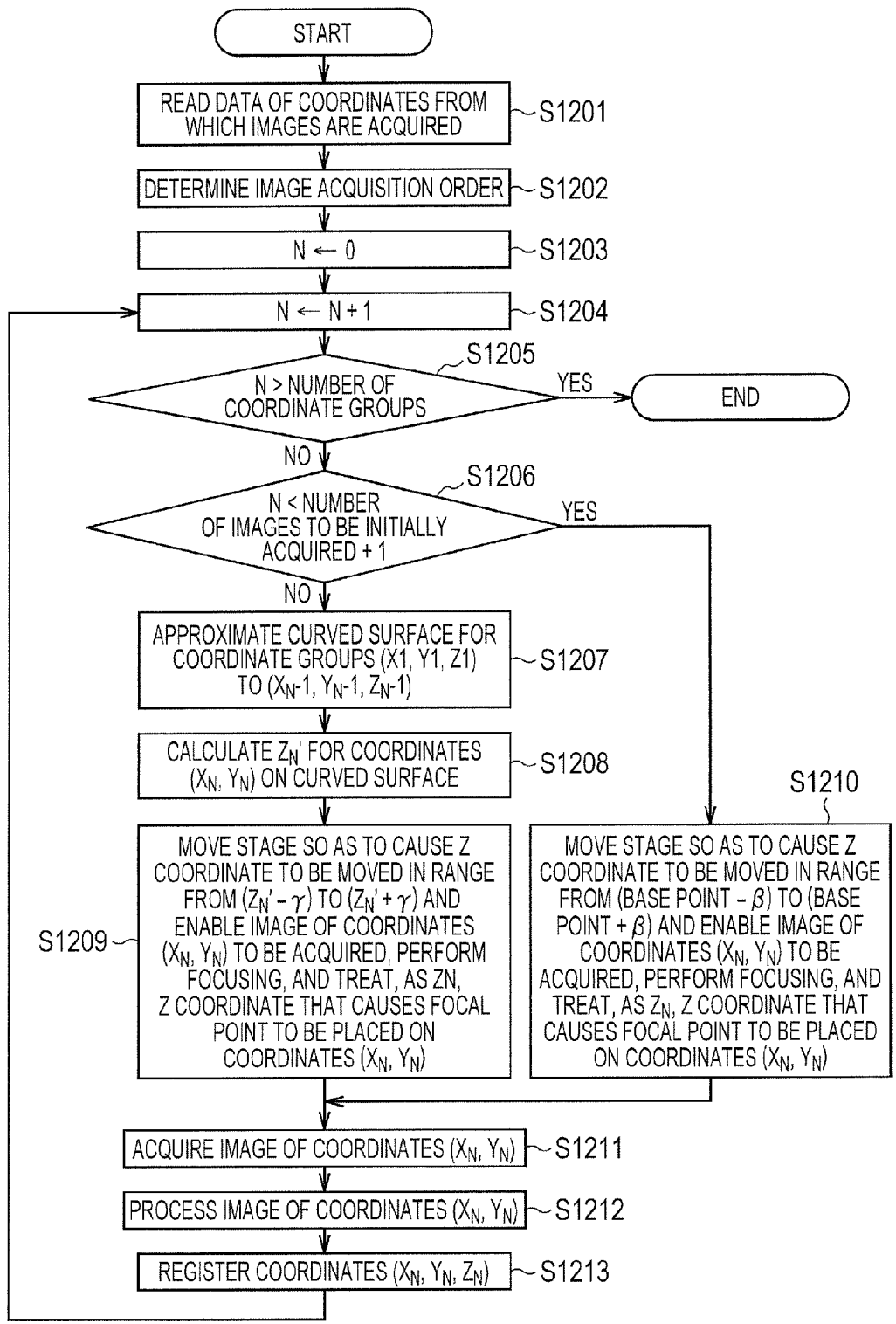
FIG. 12 is a flow diagram illustrating an example of a flowchart of the image acquisition program.

FIG. 12 is a flowchart of the image acquisition program 231 and illustrates a different example from FIG. 2. According to the image acquisition program, the image acquisition coordinate data 230 is read in step S1201, and the order of acquiring images of the coordinate groups described in the read image acquisition coordinate data 230 is determined in step S1202. Next, the variable N is substituted with zero in step S1203, and the variable N is incremented by 1 in step S1204. If the variable N exceeds the number of the coordinate groups described in the image acquisition coordinate data 230 in conditional branching step S1205, the program is terminated.

On the other hand, if the variable N does not exceed the number of the coordinate groups described in the image acquisition coordinate data 230 in conditional branching step S1205, the process proceeds to step S1206. In step S1206, the variable N is compared with the number of the images to be initially acquired, specified in step S1202, and the process proceeds to any of steps S1207 and S1210. If the variable N is smaller than a value obtained by adding 1 to the number of the images to be initially acquired, the process proceeds to step S1210. If the variable N is not smaller than the value, the process proceeds to step S1207.

Step S1210 is performed when the variable N is in the range of 1 to the number of the images to be initially acquired. In step S1210, the stage is moved so that an image of the coordinates (XN, YN) can be acquired and the Z coordinate is moved in a scanning range of (a base point−β) to (the base point+β), and the focusing is performed. The base point means an estimated value of an average Z coordinate of the surface of the substrate, and β is a fixed value that is larger than a described later. Step S1207 is performed when the variable N is equal to the value obtained by adding 1 to the number of the images to be initially acquired. In step S1207, a B-spline surface is approximated for a number N of three-dimensional coordinates from (X1, Y1, Z1) to (XN−1, YN−1, ZN−1), and the approximated curved surface is treated as a focus map.

In step S1208, a value ZN' corresponding to coordinates (XN, YN) of the approximated curved surface is calculated. The value ZN' is an estimated value of a Z coordinate that is estimated to adjust the focal point in order to acquire an image of the coordinates (XN, YN). In step S1209, the stage is moved so that an image of the coordinates (XN, YN) can be acquired and the Z coordinate is moved in a scanning range of (ZN'−γ) to (ZN'+γ), and the focusing is performed. The Z coordinate that causes the focal point to be adjusted to the coordinates (XN, YN) is regarded as ZN. The value γ can be set to a smaller value than the value β by generating a focus map and calculating ZN'. As a result, the scanning range of the Z coordinate can be reduced, and the time to complete the focusing can be reduced. In addition, the process using γ takes a shorter time than the process using α in step S309 of FIG. 2. Specifically, as the number of images to be acquired is increased, the value γ can be reduced.

In step S1211, an image of the coordinates (XN, YN) to which the focal point is adjusted is acquired. In step S1212, the acquired image is processed according to the image processing program 234, and then image processing as follows is performed. One is an image processing which includes: detecting a defect from the acquired image of the coordinates (XN, YN), extracting a characteristic amount of the defect, and classifying the defect. Other one is an image processing which includes: calculating a size of the defect or a pattern, or calculating a distance between patterns from a characteristic amount of the image. In step S1213, the three dimensional coordinates (XN, YN, ZN) are registered in the secondary storage device 216 in order to generate or update the focus map in step S1207. Then, the process returns to step S1204.

Figure 13:
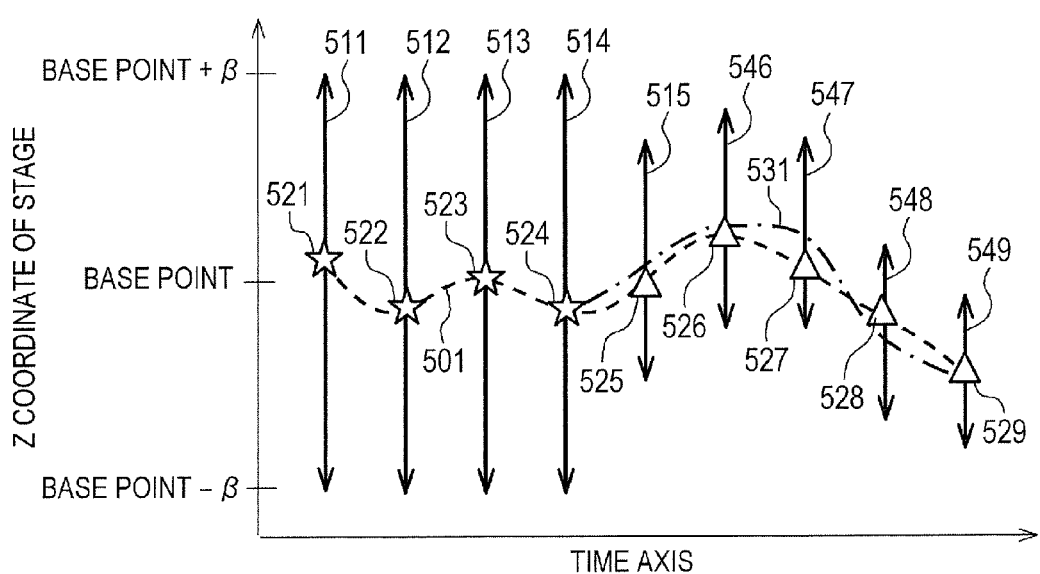
FIG. 13 is a graph illustrating an example of an outline diagram with respect to a time axis.

FIG. 13 is a schematic diagram illustrating an example of the state in which the scanning range of the Z coordinate to be moved for the focusing is changed by executing the image acquisition program described in FIG. 12. In this schematic diagram, the image acquisition coordinates are reduced to 9 coordinates for convenience of the sheet. The abscissa indicates a time axis, and the ordinate indicates the Z coordinate that is moved for the focusing. A broken line 501 indicates a Z coordinate of the surface of the substrate. Arrows from 511 to 515 and 546 to 549 that extend in the vertical direction indicate scanning ranges in Z direction for adjusting the focal point to each of the image acquisition coordinates.

After the image acquisition program 231 is executed and the image acquisition order is determined, the Z coordinate is moved in the range indicated by the arrow 511 for coordinates from which an image is acquired first, and the focusing is performed. The Z coordinate at which the focusing is completed is indicated by a star sign 521. Next, the Z coordinate is moved in the range indicated by the arrow 512 for coordinates from which an image is acquired second, and the focusing is performed. The Z coordinate at which the focusing is completed is indicated by a star sign 522. Next, the Z coordinate is moved in the range indicated by the arrow 513 for coordinates from which an image is acquired third, and the focusing is performed. The Z coordinate at which the focusing is completed is indicated by a star sign 523. Next, the Z coordinate is moved in the range indicated by the arrow 514 for coordinates from which an image is acquired fourth, and the focusing is performed. The Z coordinate at which the focusing is completed is indicated by a star sign 524. In the schematic diagram, the first to fourth image acquisition coordinates are initial coordinate groups.

Next, a curved surface is approximated using the first to fourth image acquisition coordinates and the Z coordinates indicated by the star signs 521, 522, 523, and 524. The Z coordinate on the curved surface approximated for the fifth image acquisition coordinates or the Z coordinate at which the focusing is estimated to be completed for the fifth image acquisition coordinates is estimated. Next, a range of an arrow 515 is determined for the fifth image acquisition coordinates, the Z coordinate is moved to the determined range, and the focusing is performed. The center of the arrow 515 is a Z coordinate of image acquisition coordinates corresponding to the approximated curved surface. The Z coordinate to which the focal point is adjusted on the image acquisition coordinates is indicated by a triangle 525.

Next, a curved surface is approximated using the first to fifth image acquisition coordinates and the Z coordinates indicated by the star signs 521, 522, 523, and 524 and the triangle 525. A range of an arrow 546 is determined for the sixth image acquisition coordinates, the Z coordinate is moved to the determined range, and the focusing is performed. The Z coordinate at which the focusing is completed is indicated by a triangle 526. Next, a curved surface is approximated using the first to sixth image acquisition coordinates and the Z coordinates indicated by the star signs 521, 522, 523, and 524 and the triangles 525 and 526. A range of an arrow 547 is determined for the seventh image acquisition coordinates, the Z coordinate is moved to the determined range, and the focusing is performed. The Z coordinate at which the focusing is completed is indicated by a triangle 527. Next, a curved surface is approximated using the first to seventh image acquisition coordinates and the Z coordinates indicated by the star signs 521, 522, 523, and 524 and the triangles 525, 526 and 527. A range of an arrow 548 is determined for the eighth image acquisition coordinates, the Z coordinate is moved to the determined range, and the focusing is performed. The Z coordinate at which the focusing is completed is indicated by a triangle 528. Next, a curved surface is approximated using the first to seventh image acquisition coordinates and the Z coordinates indicated by the star signs 521, 522, 523, and 524 and the triangles 525, 526, 527, and 528. A range of an arrow 549 is determined for the ninth image acquisition coordinates, the Z coordinate is moved to the determined range, and the focusing is performed. A Z coordinate at which the focusing is completed is indicated by a triangle 529.

Unlike FIG. 2, according to the image acquisition program described with reference to FIG. 12, curved surfaces are approximated using all information about Z coordinates to which the focal point have been adjusted and from which images are already acquired, before an image is acquired from new coordinates. Thus, the latter half of generating the focus map, the higher the accuracy of a focus map and the smaller the scanning range of the Z coordinate for performing the focusing. The advantageous is more remarkable as the portions to be imaged increase in number, and focusing can be achieved in a shorter time.

In the aforementioned embodiments, the focus map is updated every time the process is performed. The focus map, however, may be updated every time the process is performed a plurality of times such as 10 times or 20 times.

The invention may be embodied in other specific forms without departing from the spirit or essential characteristics thereof. The present embodiment is therefore to be considered in all respects as illustrative and not restrictive, the scope of the invention being indicated by the appended claims, rather than by the foregoing description, and all changes which come within the meaning and range of equivalency of the claims are therefore intended to be embraced therein.

DESCRIPTION OF THE CODES

201 . . . electron source 202 . . . acceleration electrode 203 . . . focusing lens 204 . . . deflector 205 . . . objective lens 206 . . . substrate (wafer) 207 . . . driving stage 208 . . . primary electron 209 . . . secondary electron 210 . . . detector 211 . . . A/D converter 213 . . . overall controller 214 . . . CPU 215 . . . primary storage device 216 . . . secondary storage device 217 . . . output unit 218 . . . bus 219 . . . reflected electron 220a,220b . . . reflected electron detector 320 . . . substrate 321 . . . notch 501 . . . surface of the substrate

What is claimed is:

1. A defect inspection device comprising:
    a scanning electron microscope that irradiates a sample with a focused electron beam, performs scanning, and thereby acquires an SEM image of the sample;
    image processing unit which processes the SEM image acquired by imaging the sample with the scanning electron microscope;
    output unit which outputs, on a screen, a result of processing the SEM image of the sample with the image processing unit; and
    control unit which controls the scanning electron microscope, the image processing unit, and the output unit, wherein, when the control unit controls the scanning electron microscope for sequentially imaging a plurality of portions on the sample, the control unit causes the scanning electron microscope:
    in a first predetermined number of portions, to perform the scanning by moving a focal point of the electron beam in a normal direction relative to a surface of the sample in a predetermined range; to adjust the focal point of the electron beam to the surface of the sample; and
    to image the sample;
    then, to estimate a curved surface shape of the surface of the sample by using information about positions to which the focal point of the electron beam has been adjusted on the surface of the sample in the first predetermined number of portions;
    after imaging the sample in the first predetermined number of portions, to use information about the estimated curved surface to perform the scanning by moving the focal point of the electron beam in the normal direction in a narrower range than the predetermined range for the scanning that has been performed in the first predetermined number of portions in order to adjust the focal point of the electron beam to the surface of the sample;
    to adjust the focal point of the electron beam to the surface of the sample; and to image the sample, wherein the control unit performs controls for using the information about the estimated curved surface to perform the scanning in a narrower range than the predetermined range for the scanning that has been performed for the first predetermined number of portions, and correcting the estimated curved surface shape of the sample by using the information about the positions to which the focal point of the electron beam has been adjusted on the surface of the sample in the first predetermined number of portions.

2. The defect inspection device according to claim 1,
    wherein the control unit performs controls for setting the first predetermined number of portions on the sample, performing the scanning on each of the set portions by moving the focal point of the electron beam in the normal direction relative to the surface of the sample in a predetermined range, adjusting the focal point of the electron beam to the surface of the sample, and imaging the sample.

3. The defect inspection device according to claim 1,
    wherein the control unit performs controls for estimating the curved surface shape of the surface of the sample by approximating a B-spline surface by using the information about the positions to which the focal point of the electron beam has been adjusted on the surface of the sample in the first predetermined number of portions.

4. The defect inspection device according to claim 1,
    wherein the output unit outputs the estimated curved surface shape of the surface of the sample on the screen for displaying purpose.

5. A defect inspection method comprising the steps of:
    sequentially acquiring SEM images of a plurality of portions on a sample by irradiating the plurality of portions on a sample with an electron beam focused by a scanning electron microscope to perform scanning;
    processing the SEM images obtained by sequentially imaging the plurality of portions on the sample with the scanning electron microscope and inspecting the sample; and
    outputting a result of processing the SEM images of the sample, wherein the sequential acquisition of the SEM images of the plurality of portions on the sample with the scanning electron microscope includes the steps of:

performing the scanning for a first predetermined number of portions by moving a focal point of the electron beam in a normal direction relative to a surface of the sample in a predetermined range, adjusting the focal point of the electron beam to the surface of the sample, and imaging the sample;

estimating a curved surface shape of the surface of the sample by using information about positions to which the focal point of the electron beam has been adjusted on the surface of the sample in the first predetermined number of portions; and after imaging the sample in the first predetermined number of portions, using information about the estimated curved surface to perform the scanning by moving the focal point of the electron beam in the normal direction in a narrower range than the predetermined range for the scanning that has been performed in the first predetermined number of portions in order to adjust the focal point of the electron beam to the surface of the sample, adjusting the focal point of the electron beam to the surface of the sample, and imaging the sample, wherein the scanning is performed using the information about the estimated curved surface in a narrower range than the predetermined range for the scanning that has been performed in the first predetermined number of portions, and the estimated curved surface shape of the sample is corrected by using the information about the positions to which the focal point of the electron beam has been adjusted on the surface of the sample in the first predetermined number of portions.

6. The defect inspection method according to claim 5, wherein the first predetermined number of portions on the sample are set on the basis of data stored in advance, the scanning is performed by moving the focal point in the normal direction relative to the surface in a predetermined range in order to adjust the focal point of the electron beam on each of the set portions, the focal point of the electron beam is adjusted to the surface of the sample, and the sample is imaged.

7. The defect inspection method according to claim 5, wherein the curved surface shape of the surface of the sample is estimated by approximating a B-spline surface using the information about the positions to which the focal point of the electron beam has been adjusted on the surface of the sample in the first predetermined number of portions.

8. The defect inspection method according to claim 5, wherein the estimated curved shape of the surface of the sample is displayed on the screen.

9. A defect inspection method comprising the steps of:
sequentially acquiring SEM images of a plurality of portions on a sample by sequentially performing:

on a plurality of portions of the surface of the sample, scanning with a focal point of an electron beam focused by a scanning electron microscope, the focal point adjusted to a surface of a sample; and imaging the sample;

processing the sequentially acquired SEM images of the plurality of portions on the sample and inspecting the sample; and outputting results of the inspection, wherein the adjusting of the focal point of the electron beam focused by the scanning electron microscope on the surface of the sample includes the steps of:

performing the scanning in a first predetermined number of portions by moving the focal point of the electron beam in a normal direction relative to the surface of the sample in a predetermined range, adjusting the focal point of the electron beam to the surface of the sample, and imaging the sample;

estimating a curved surface shape of the surface of the sample by using information about positions to which the focal point of the electron beam has been adjusted on the surface of the sample in the first predetermined number of portions; and after imaging the sample in the first predetermined number of portions, performing the scanning by moving the focal point of the electron beam in a narrower range than the predetermined range in which scanning has been performed in the first predetermined number of portions using information indicating that the focal point of the electron beam has been adjusted to the surface of the sample for each of the first predetermined number of portions, adjusting the focal point of the electron beam on the surface of the sample, and imaging the sample.

10. The defect inspection method according to claim 9, wherein when the sample is to be imaged after the imaging of the first predetermined number of portions, information about the positions at which the focal point of the electron beam has been adjusted on the surface of the sample before the imaging of the sample is used to perform the scanning by moving the focal point of the electron beam in a range that is the same as or narrower than a certain range for the scanning that has been performed by moving the focal point of the electron beam in the certain range in order to adjust the focal point of the electron beam on the surface of the sample before the imaging of the sample, and the focal point of the electron beam is adjusted on the surface of the sample.

11. The defect inspection method according to claim 9, wherein the first predetermined number of portions are portions specified on the sample in advance.

* * * * *